United States Patent
Gong et al.

(10) Patent No.: US 11,498,058 B2
(45) Date of Patent: Nov. 15, 2022

(54) SUPPORTED PTZN INTERMETALLIC ALLOY CATALYST, METHOD FOR PREPARING THE SAME AND APPLICATION THEREOF

(71) Applicant: Tianjin University, Tianjin (CN)

(72) Inventors: Jinlong Gong, Tianjin (CN); Sai Chen, Tianjin (CN); Liang Zeng, Tianjin (CN)

(73) Assignee: Tianjin University, Tianjin (CN)

(*) Notice: Subject to any disclaimer, the term of this patent is extended or adjusted under 35 U.S.C. 154(b) by 0 days.

(21) Appl. No.: 17/260,559

(22) PCT Filed: Nov. 21, 2019

(86) PCT No.: PCT/CN2019/119858
§ 371 (c)(1),
(2) Date: Jan. 15, 2021

(87) PCT Pub. No.: WO2020/143338
PCT Pub. Date: Jul. 16, 2020

(65) Prior Publication Data
US 2021/0322956 A1    Oct. 21, 2021

(30) Foreign Application Priority Data

Jan. 8, 2019    (CN) .......................... 201910013796.7

(51) Int. Cl.
*C07C 5/333*    (2006.01)
*B01J 23/60*    (2006.01)
(Continued)

(52) U.S. Cl.
CPC ............. *B01J 23/60* (2013.01); *B01J 8/0285* (2013.01); *B01J 21/04* (2013.01); *B01J 21/08* (2013.01);
(Continued)

(58) Field of Classification Search
CPC ... B01J 23/60; B01J 8/02; B01J 8/0285; B01J 21/04; B01J 21/08; B01J 35/002;
(Continued)

(56) References Cited

U.S. PATENT DOCUMENTS 5,346,871 A * 9/1994 Robbins ................. C07C 5/325
502/238
8,338,654 B2 * 12/2012 Giedigkeit ............... B01J 23/60
585/277

FOREIGN PATENT DOCUMENTS

CN         105521779 A *    4/2016

OTHER PUBLICATIONS

Gallagher et al. ("Structural evolution of an intermetallic Pd—Zn catalyst selective for propane dehydrogenation". Phys. Chem. Chem. Phys., 2015, 17, 28144) (Year: 2015).*

* cited by examiner

*Primary Examiner* — In Suk C Bullock
*Assistant Examiner* — Jason Y Chong
(74) *Attorney, Agent, or Firm* — George G. Wang; Bei & Ocean (57) ABSTRACT

The present application discloses a supported PtZn intermetallic alloy catalyst, a method for preparing the same and application thereof. The catalyst uses $SiO_2$ as a support and Zn as a promoter, and a small amount of active component Pt is supported; the weight percentage of Pt is 0.025%-1%, and the weight percentage of Zn is 0.025%-1.7%, a co-impregnation method is adopted in preparation, the $SiO_2$ support is impregnated in aqueous solution of chloroplatinic acid and zinc nitrate, and then drying and high-temperature reduction are performed to obtain a $PtZn/SiO_2$ catalyst. The catalyst has the advantages of high activity, high stability, low price and low toxicity. The catalyst provided by the present application is applicable to preparation of alkene (Continued)

through short-chain alkane dehydrogenation, in particular to preparation of propylene through propane dehydrogenation in a hydrogen atmosphere. Under high-temperature conditions, the dehydrogenation activity is very high, the propylene selectivity can reach more than 90%, the stability is good, and the amount of used Pt is small, the utilization rate is high, and it is cheaper than industrial Pt series catalysts.

5 Claims, 5 Drawing Sheets

(51) Int. Cl.
*B01J 8/02* (2006.01)
*B01J 21/04* (2006.01)
*B01J 21/08* (2006.01)
*B01J 35/02* (2006.01)
*B01J 37/02* (2006.01)
*B01J 37/08* (2006.01)
*B01J 37/18* (2006.01)

(52) U.S. Cl.
CPC ........... *B01J 35/023* (2013.01); *B01J 35/026* (2013.01); *B01J 37/0201* (2013.01); *B01J 37/08* (2013.01); *B01J 37/18* (2013.01); *C07C 5/3337* (2013.01); *C07C 2521/04* (2013.01); *C07C 2521/08* (2013.01); *C07C 2523/60* (2013.01)

(58) Field of Classification Search
CPC .... B01J 35/023; B01J 35/026; B01J 37/0009; B01J 37/0063; B01J 37/0201; B01J 37/08; B01J 37/18; Y02P 20/52
See application file for complete search history.

SUPPORTED PTZN INTERMETALLIC ALLOY CATALYST, METHOD FOR PREPARING THE SAME AND APPLICATION THEREOF

TECHNICAL FIELD

The present application relates to a supported catalyst, in particular to a $SiO_2$ supported PtZn intermetallic alloy catalyst, a method for preparing the same and application of the catalyst to preparation of alkene through low-carbon alkane dehydrogenation (taking preparation of propylene through propane dehydrogenation as an example).

BACKGROUND OF THE PRESENT INVENTION

Short-chain alkenes (such as ethylene, propylene, butane and butadiene) are basic raw materials in the chemical industry. Especially, propylene is in a great demand in recent years. Propylene is a basic raw material for making three major synthesized materials and is mainly used to produce acrylonitrile, acetone, propylene oxide and other products. At present, propylene supply mainly comes from byproducts of processes of ethylene preparation through naphtha cracking and of petroleum catalytic cracking. However, with the development of shale gas technology, ethane becomes increasingly cheaper and easier to obtain. Ethylene production process starts to change from naphtha cracking to ethane steam cracking, so the supply of propylene is restricted and the price is also rising. Due to high energy consumption, low selectivity and shortage of petroleum resources, people are looking for more economical and efficient production methods of short-chain alkenes such as propylene. Due to large price difference between propane and propylene, propane dehydrogenation (PDH) process has attracted more and more attention in recent years. In October 2013, a propane dehydrogenation unit with an annual capacity of 600,000 tons was put into operation in Tianjin Bohai Chemical Industry Group Co., Ltd., and the propane dehydrogenation production was officially started in China. During 2014-2016, the production capacity of propane dehydrogenation (including mixed alkane) had increased at the speed of at least three units put into operation per year. By the end of 2017, China's total production capacity of propane dehydrogenation (including mixed alkane) reached 5,135,000 tons, accounting for 15% of the total capacity.

The reaction formula of propane dehydrogenation is $C_3H_8 \leftrightarrows C_3H_6 + H_2$, $\Delta H_{298K} = 124.3$ kJ/mol. Since propane catalytic dehydrogenation is a strong endothermic reaction, controlled by thermodynamic equilibrium, high temperature and low pressure conditions are conducive to the reaction. At present, there are five major techniques for propane dehydrogenation, including Catofin (Lummus), Oleflex (UOP), STAR (UHDE), FBD (Snamprogetti and Yarsintez) and Linde-BASF PDH. All of these techniques use Pt series and Cr series catalysts. Wherein, Catofin (Lummus) and Oleflex (UOP) are the two most widely used techniques. In the Catofin process, a Cr series catalyst and a fixed bed reactor are used, the catalyst is regenerated once in 12 minutes, the single-pass conversion rate is 55%-60% and the selectivity is 90%. In the Oleflex process, a Pt series catalyst and a moving bed reactor are used, fully continuous operation is realized, the single-pass conversion rate is about 35%-40% and the selectivity is 84%. The two major catalysts are seriously deactivated due to carbon deposition, so they need to be regenerated. Moreover, chromium is highly toxic and harmful to the environment, while platinum is expensive, which seriously restricts the development of propane dehydrogenation process. Therefore, it is of great practical significance to find a cheap, low-toxicity, high-activity and high-stability PDH catalyst to reduce the amount of used Pt.

Dehydrogenation reaction of low-carbon alkanes is structurally insensitive, which means that monoatomic Pt can catalyze the dehydrogenation reaction. However, for side reactions associated with low-carbon alkane dehydrogenation, such as hydrolysis, isomerization and carbon deposition, these side reactions are structurally sensitive. The larger the particle size of Pt, the more favorable these side reactions occur (Molecular understandings on the activation of light hydrocarbons over heterogeneous catalysts. Chemical Science 2015, 6 (8), 4403-4425). Therefore, using single-site Pt as an active site for low-carbon alkane dehydrogenation is expected to achieve high selectivity in the production of low-carbon alkenes. Intermetallic alloy is a kind of bimetallic alloy, in which the metal with catalytic activity is separated by inert metal atoms in the form of single atom. It is widely applied to low-temperature electrocatalytic reaction, but its application to high-temperature low-carbon alkane dehydrogenation reaction is rarely reported.

SUMMARY OF THE PRESENT INVENTION

The purpose of the present application is to overcome the defects of the prior art, aim at solving the technical problems that the existing Pt catalyst is easily deposited with carbon and the amount of used precious metal is great, and provide a supported PtZn intermetallic alloy catalyst, a method for preparing the same and application thereof to propane dehydrogenation. The catalyst has high activity, high stability, ultra-low previous metal content and low deactivation rate in catalytic dehydrogenation, and can improve the yield of propylene.

The present application is implemented by adopting the following technical solution.

Provided is a supported PtZn intermetallic alloy catalyst, which uses Pt as an active component and Zn as a promoter supported on a support. Pt and Zn form an atomically ordered intermetallic alloy. Based on the weight of the support in the catalyst (100 wt %), the weight percentage of Pt is no more than 1% ((weight of metal Pt)/(weight of support)*100 wt %), and the weight percentage of Zn is no more than 1.7% ((weight of metal Zn)/(weight of support)*100 wt %).

The support is one selected from the group consisting of silicon dioxide, molecular sieve, zeolite, and aluminum oxide.

The weight percentage of Pt is 0.025 wt %-1 wt %, preferably 0.1 wt %-0.5 wt %.

The weight percentage of Zn is 0.025 wt %-1.5 wt %, preferably 0.17 wt %-0.85 wt %.

Pt and Zn atoms are arranged in order in a spaced manner to form an atomically ordered intermetallic alloy.

Provided is a method for preparing the catalyst, which includes:

Step 1: putting a support in solution containing metal platinum and metal zinc precursors for impregnation such that the metal platinum and the metal zinc are supported on the support.

In step 1, soluble zinc salt and chloroplatinic acid are selected to respectively provide the metal zinc and the metal platinum, and are evenly dispersed in deionized water;

wherein, the soluble zinc salt is one selected from the group consisting of zinc nitrate, zinc chloride, and zinc sulfate.

In step 1, the support is one selected from the group consisting of silicon dioxide, molecular sieve, zeolite, and aluminum oxide.

In step 1, the amount of the support is 1 part by weight, the amount of the metal platinum is 0.0025-0.01 part by weight, the amount of metal zinc is 0.0025-0.017 part by weight, each part by weight is 1 g, and equal-volume impregnation may be selected.

In step 1, ultrasonic dispersion is selected during impregnation, the ultrasonic dispersion time is 0.5 h-1 h, natural drying is performed for 10-12 h at room temperature of 20-25° C. after impregnation, and then complete drying is performed at the temperature ranges from 80° C. to 120° C.

Step 2: placing the support on which the metal platinum and the metal zinc are supported in step 1 in a hydrogen atmosphere for reduction at reduction (heat preserving) temperature ranges from 400° C. to 700° C. to obtain the supported PtZn intermetallic alloy catalyst.

In step 2, the reduction temperature is 500-600° C.

In step 2, the reduction time is 0.5-3 h, preferably 0.5-1 h.

In step 2, the temperature is increased from room temperature of 20-25° C. to reduction temperature at the speed of 5-10° C. per minute, then heat preservation is performed, and then natural cooling to room temperature of 20-25° C. is performed. In the whole process, the support on which the metal platinum and the metal zinc are supported is always in the hydrogen atmosphere, and hydrogen is extracted after cooling to room temperature is completed.

Provided is application of the supported PtZn intermetallic alloy catalyst provided by the present application to preparation of short-chain alkene through short-chain alkane dehydrogenation, in particular to preparation of propylene through propane dehydrogenation. The following steps are performed.

The supported PtZn intermetallic alloy catalyst is tabletted into a granular catalyst, the granular catalyst with a mesh size of 20-40 meshes is selected and used, then the obtained granular catalyst is contained into a fixed bed reactor, nitrogen is fed, and the temperature is increased to pretreatment temperature of 500-700° C.; hydrogen is fed for pretreatment, the temperature is maintained at the pretreatment temperature for 0.5 h-1 h, and the temperature is tuned to reaction temperature of 500-650° C.; a reaction gas is fed for reaction; wherein, the molar ratio of hydrogen to propane is (0-2):1, nitrogen is an equilibrium gas, the total gas amount is kept unchanged, and the reaction space velocity based on propane is 1-5 $h^{-1}$.

The temperature of pretreatment by using hydrogen is 600-700° C.; the reaction temperature is 600-650° C.; the molar ratio of hydrogen to propane is 1:1, and the reaction space velocity based on propane is 3-4 $h^{-1}$. The supported PtZn intermetallic alloy catalyst provided by the present application has a high specific surface area and mesopore, which is conducive to the uniform distribution of the active component and the diffusion of gas molecules; since a small amount of Pt is used as the active component (0.025%-1 wt %, the content of Pt in the industrial Pt catalyst is more than 0.5 wt %), the content of Pt in the catalyst is decreased and the cost of the catalyst is reduced; since Pt and Zn form an atomically ordered intermetallic alloy such that Pt and Zn atoms are spaced in order, on the one hand, the utilization ratio of Pt atoms is greatly improved; on the other hand, the desorption of the product propylene is promoted, the side reactions such as C—C bond breaking and deep dehydrogenation are inhibited, and the activity, selectivity and stability of the catalyst are greatly improved. The catalyst provided by the present application is prepared by adopting a co-impregnation method, the raw materials can be easily obtained, the process is simple, the repeatability is high, and it has certain industrial significance. The catalyst provided by the present application is applicable to preparation of propylene through propane dehydrogenation in a hydrogen atmosphere, the effect is good, the dehydrogenation activity under high temperature conditions is very high, the propylene selectivity can reach more than 90%, and the stability is good.

DETAILED DESCRIPTION OF THE PRESENT INVENTION

The present application will be further described below in detail through specific examples. The following examples can allow those skilled in the art to more comprehensively understand the present application, rather than to limit the present application in any form.

Embodiment 1

Step (1) 0.0021 g of $H_2PtCl_6$ and 0.078 g of $Zn(NO_3)_2 \cdot 6H_2O$ were dissolved in 4 ml deionized water to prepare a solution;

Step (2) 1.0000 g of $SiO_2$ (or $Al_2O_3$) was impregnated in the prepared solution, ultrasonic treatment was performed for 0.5 h, and drying was performed for 12 h at room temperature, and drying was performed at 100° C. until completely dried;

Step (3) the solid obtained in the step (2) was reduced for 1 h at 600° C. to obtain a $PtZn/SiO_2$ (or $PtZn/Al_2O_3$) catalyst. Based on the weight of the support in the catalyst, the weight percentage of Pt was 0.1 wt % and the mass percentage of Zn was 0.17 wt %;

Step (4) the prepared $SiO_2$ (or $Al_2O_3$) supported intermetallic catalyst was tableted to obtain a 20-mesh to 40-mesh granular catalyst;

Step (5) the tableted $SiO_2$ (or $Al_2O_3$) supported intermetallic granular catalyst was contained into a fixed bed reactor, nitrogen was fed, and the temperature was increased to 600° C.; hydrogen was fed for pretreatment, and the temperature was kept for 1 h at 600° C.; the reaction temperature was 600° C., the weight hourly space velocity of propane was 4 $h^{-1}$, the molar ratio of hydrogen to propane in the reaction gas was 1:1 and the equilibrium gas was nitrogen.

The activity of the catalyst was expressed by propane conversion rate, propylene selectivity and deactivation rate. The propylene selectivity and deactivation rate were calculated as follows:

Selectivity:

$$Sel(\%) = \frac{[F_{C_3H_6}]_{out}}{[F_{C_3H_8}]_{in} - [F_{C_3H_8}]_{out}} \times 100$$

Conversion rate:

$$Con(\%) = \frac{[F_{C_3H_8}]_{in} - [F_{C_3H_8}]_{out}}{[F_{C_3H_8}]_{in}} \times 100$$

Deactivation rate:

$$k_d = \left[\ln\left(\frac{1-X_{final}}{X_{final}}\right) - \ln\left(\frac{1-X_{initial}}{X_{initial}}\right)\right] / t$$

where $[F_{C_3H_8}]_{in}$ represents volume flow rate of propane at a reactor inlet, $[F_{C_3H_8}]_{out}$ and $[F_{C_3H_6}]_{out}$ respectively represent gas volume flow rates of propane and propylene at a reactor outlet, $X_{initial}$ and $X_{final}$ respectively represent propane conversion rates at beginning and end of reaction.

Figure 1:
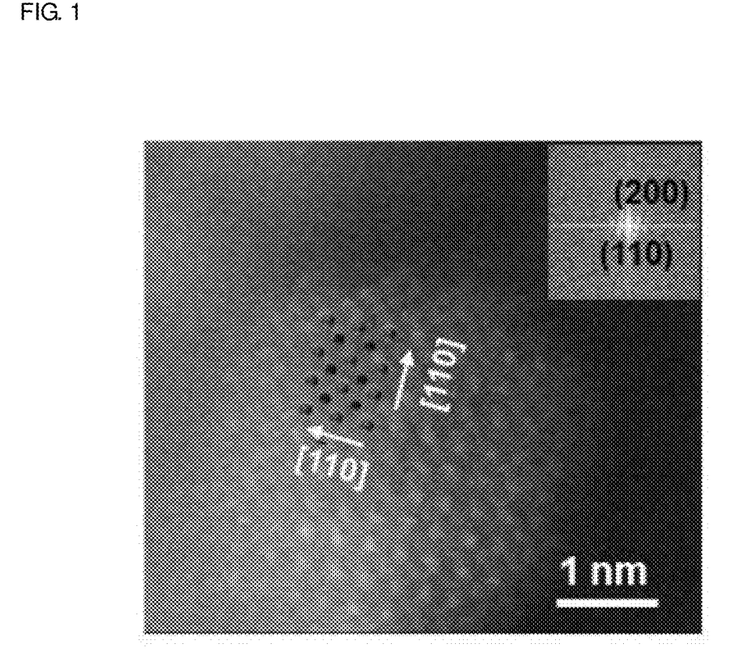
FIG. 1 illustrates an AC-HAADF-TEM photo of a $SiO_2$ supported PtZn intermetallic alloy catalyst prepared in embodiment 1 according to the present application.
Figure 2:
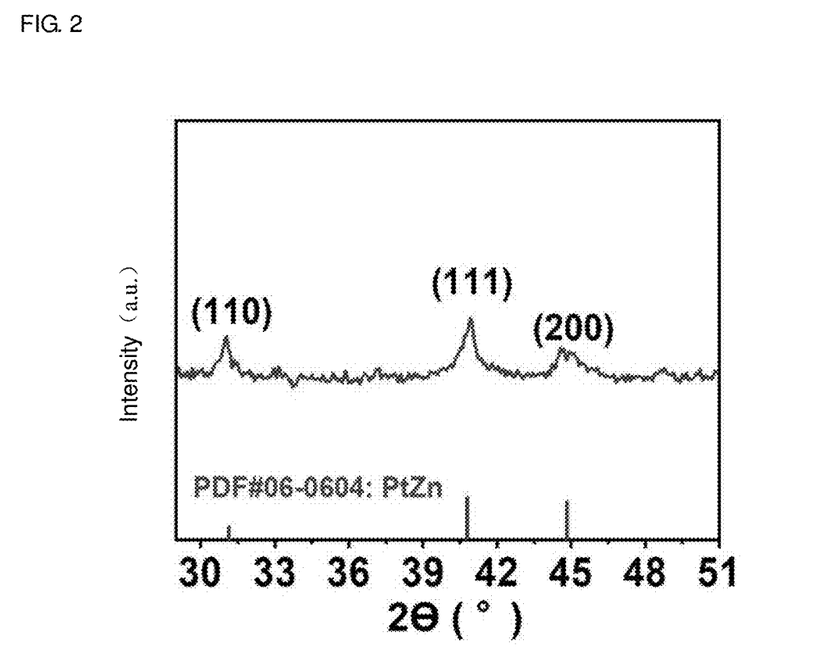
FIG. 2 illustrates an XRD spectrum of a $SiO_2$ supported PtZn intermetallic alloy catalyst prepared in embodiment 1 according to the present application.

FIG. 1 illustrates an AC-HAADF-TEM photo of the $PtZn/SiO_2$ catalyst prepared in the Embodiment 1, from which it can be seen that Pt and Zn atoms are arranged in order in a spaced manner, while the PtZn monoatomic alloy is attached to the surface of the $SiO_2$ support. FIG. 2 illustrates an XRD curve chart of the $PtZn/SiO_2$ catalyst prepared in the Embodiment 1, showing the crystal phase structure of the PtZn intermetallic alloy.

Figure 3:
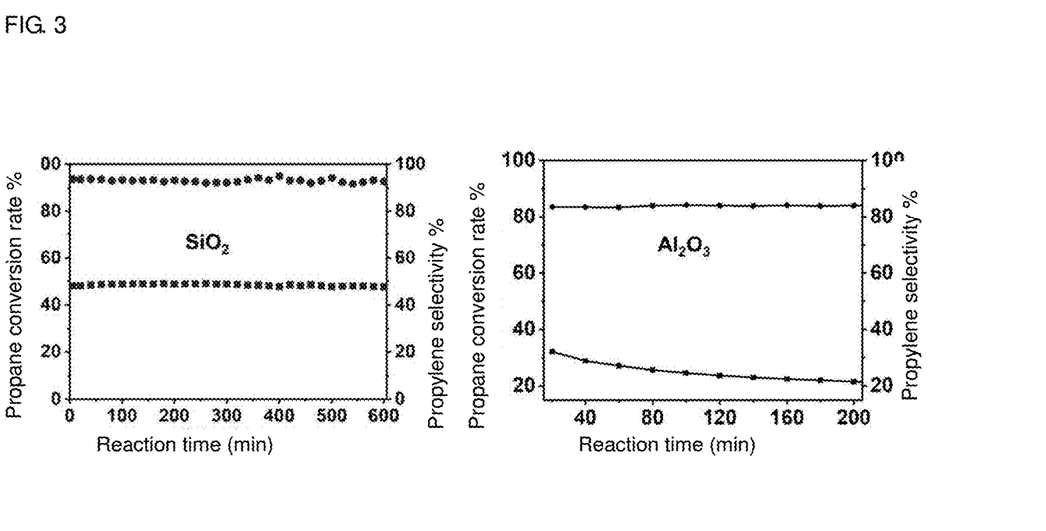
FIG. 3 illustrates an activity test curve chart of PtZn intermetallic alloy catalysts supported by respectively using $SiO_2$ and $Al_2O_3$ in embodiment 1 according to the present application, wherein a curve above a chemical formula corresponds to propylene selectivity and a curve below the chemical formula corresponds to propane conversion rate.

Reaction products were analyzed online by adopting gas chromatography. A relationship between propane conversion rate and propylene selectivity as the reaction time is illustrated in FIG. 3. It can be seen that, for the catalyst using silicon dioxide as the support, the propane conversion rate is 48.1% at the beginning and 47.8% after 10 h, the deactivation rate is only 0.0028 $h^{-1}$, and the propylene selectivity always remains at a high level (>94%); for the catalyst using aluminum oxide as the support, the propane conversion rate and the propylene selectivity are not as good as the former.

Embodiment 2

The method in the embodiment 1 was used for preparation and reaction, and the difference was only that the weight of zinc nitrate ($Zn(NO_3)_2 \cdot 6H_2O$) in step (1) was 0.026 g; based on the weight of the support, the weight percentage of Zn in the obtained catalyst was 0.06 wt %.

Embodiment 3

The method in the embodiment 1 was used for preparation and reaction, and the difference was only that the weight of zinc nitrate ($Zn(NO_3)_2 \cdot 6H_2O$) in step (1) was 0.234 g; based on the weight of the support, the weight percentage of Zn in the obtained catalyst was 0.5 wt %.

Embodiment 4

The method in the embodiment 1 was used for preparation and reaction, and the difference was only that the weight of $H_2PtCl_6$ in step (1) was 0.0011 g; based on the weight of the support, the weight percentage of Pt in the obtained catalyst was 0.05 wt %.

Embodiment 5

The method in the embodiment 1 was used for preparation and reaction, and the difference was only that the weight of $H_2PtCl_6$ in step (1) was 0.007 g; based on the weight of the support, the weight percentage of Pt in the obtained catalyst was 0.3 wt %.

Embodiment 6

The method in the embodiment 1 was used for preparation and reaction, and the difference was only that the reduction temperature in step (3) was 300° C.

Embodiment 7

The method in the embodiment 1 was used for preparation and reaction, and the difference was only that the reaction temperature in step (5) was 520° C.

Embodiment 8

The method in the embodiment 1 was used for preparation and reaction, and the difference was only that the reaction temperature in step (5) was 550° C.

Embodiment 9

The method in the embodiment 1 was used for preparation and reaction, and the difference was only that the reaction temperature in step (5) was 620° C.

Embodiment 10

The method in the embodiment 1 was used for preparation and reaction, and the difference was only that the weight hourly space velocity of propane in step (5) was 9.5 $h^{-1}$.

Embodiment 11

The method in the embodiment 1 was used for preparation and reaction, and the difference was only that the ratio of hydrogen to propane in step (5) was 0.

Embodiment 12

The method in the embodiment 1 was used for preparation and reaction, and the difference was only that the ratio of hydrogen to propane in step (5) was 0.5.

Embodiment 13

The method in the embodiment 1 was used for preparation and reaction, and the difference was only that the ratio of hydrogen to propane in step (5) was 2.

For the results of the above embodiments, the activity data at the beginning and at 10 h of the reaction were compared. The test conditions and methods were the same as those in the embodiment 1 (using silicon dioxide as support) to investigate the influence of different parameters on the reaction performance of the catalyst.

Figure 4:
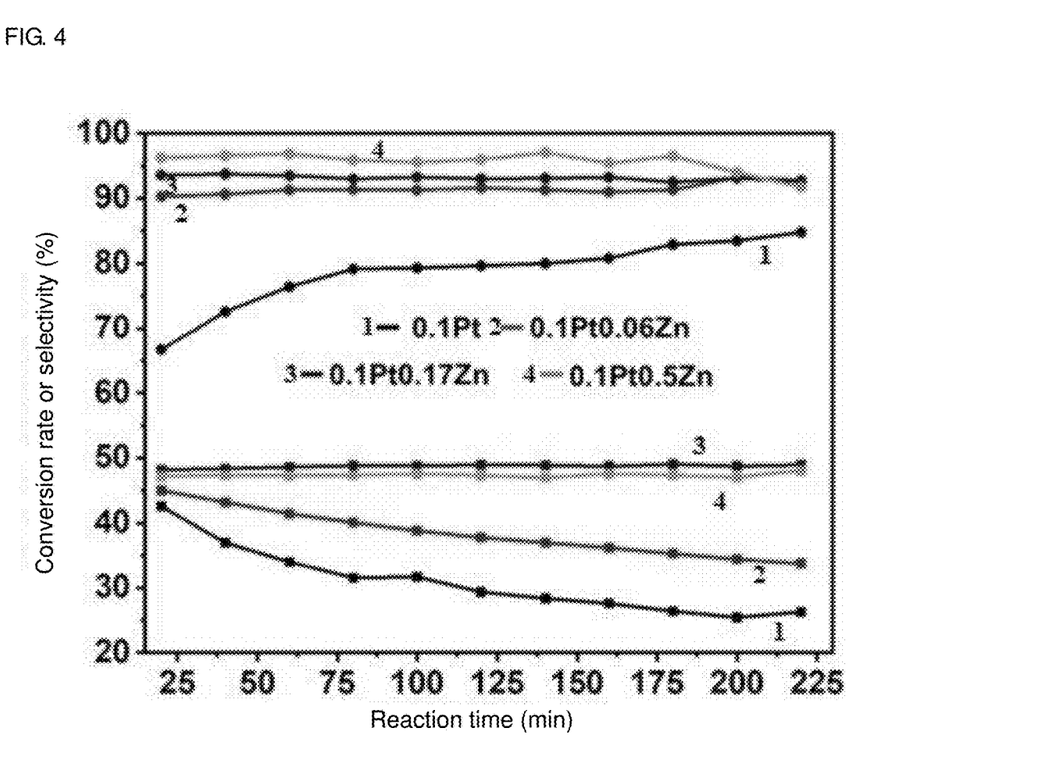
FIG. 4 illustrates a test curve chart of influence of different Zn weight percentages on catalytic activity, in the embodiments of the present application wherein curves at an upper position correspond to propylene selectivity and curves at a lower position correspond to propane conversion rate.

(1) For the influence of the weight percentage of Zn (based on the weight of the support in the catalyst) on the reaction activity of the PtZn/SiO$_2$ catalyst, refer to FIG. 4. The reaction conditions are the same as those in the embodiments 1, 2 and 3. It can be seen from FIG. 4 that when the weight percentage of Zn is 0.06-0.5 wt %, the catalyst achieves high stability and activity at the same time. The propane conversion rate at the beginning is about 48%, the selectivity is about 96%, and the deactivation rate is about 0.0028 $h^{-1}$. The reaction conditions are the same as those in the embodiments 1, 4 and 5.

Figure 5:
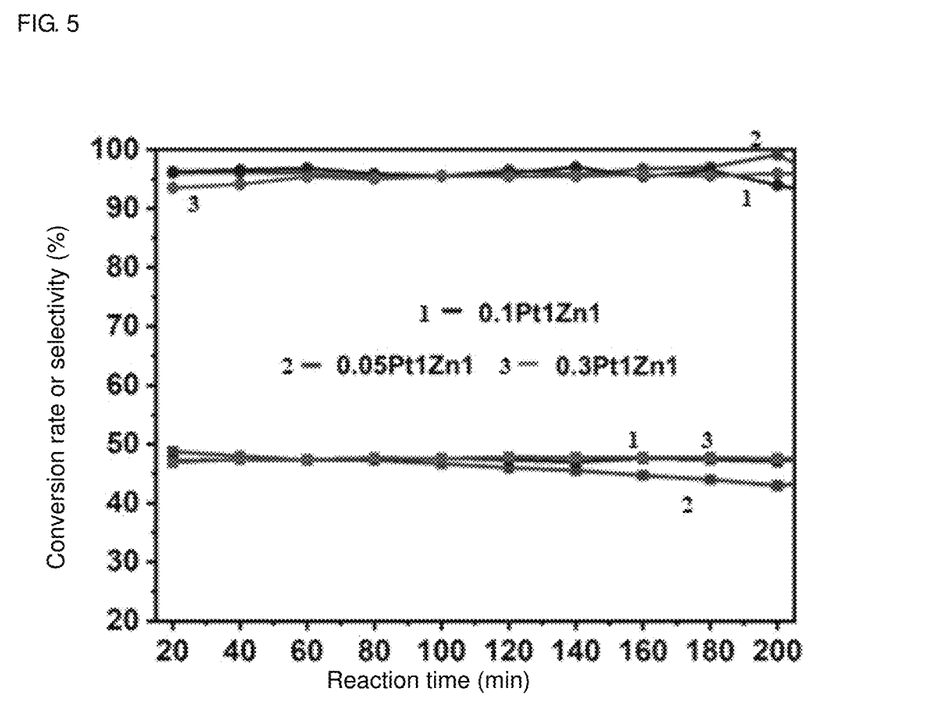
FIG. 5 illustrates a test curve chart of influence of different Pt contents on catalytic activity in the embodiments of the present application, wherein curves at an upper position correspond to propylene selectivity and curves at a lower position correspond to propane conversion rate.

(2) For the influence of the weight percentage of Pt (based on the weight of the support in the catalyst) on the reaction activity of the PtZn/SiO$_2$ catalyst, refer to FIG. 5. The reaction conditions are the same as those in the embodiments 1, 4 and 5. It can be seen from FIG. 5 that when the weight percentage of Pt is 0.05 wt %, the activity is good but the stability is poor. When the weight percentage of Pt is moderate (0.1 wt %), the catalyst can achieve very good activity and stability at the same time. The propane conversion rate at the beginning is 48%, the selectivity is 95%, and the deactivation rate is only 0.014 $h^{-1}$.

Figure 6:
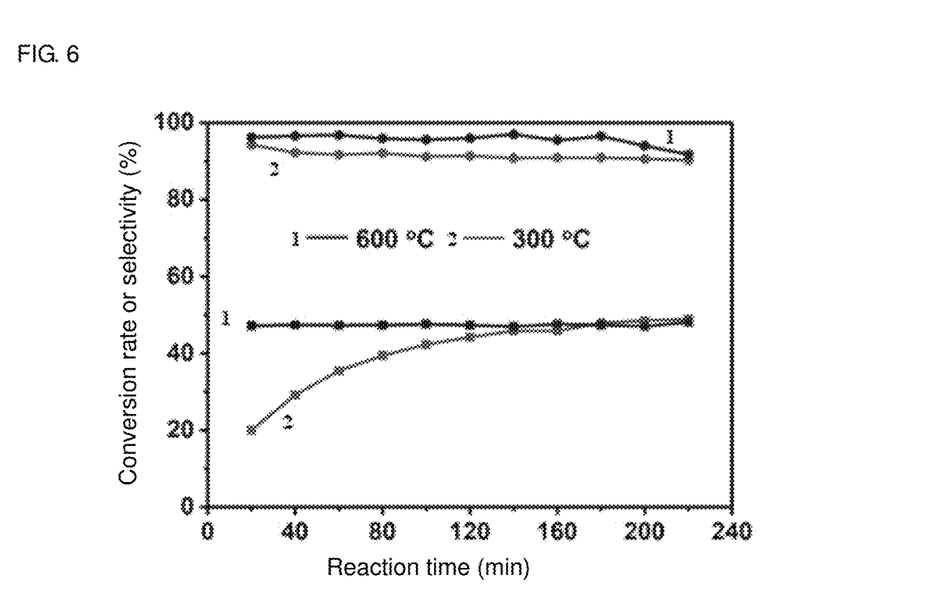
FIG. 6 illustrates a test curve chart of influence of different pre-reduction temperature on catalytic activity in the embodiments of the present application, wherein curves at an upper position correspond to propylene selectivity and curves at a lower position correspond to propane conversion rate.

(3) For the influence of the pre-reduction temperature on the reaction activity of the PtZn/SiO$_2$ catalyst, refer to FIG. 6. The reaction conditions are the same as those in the embodiments 1 and 6. It can be seen from FIG. 6 that the pre-reduction temperature has an important influence on the reaction activity and selectivity. High-temperature reduction is the necessary condition for the formation of the intermetallic alloy, and the reduction temperature is preferably 600° C.

Figure 7:
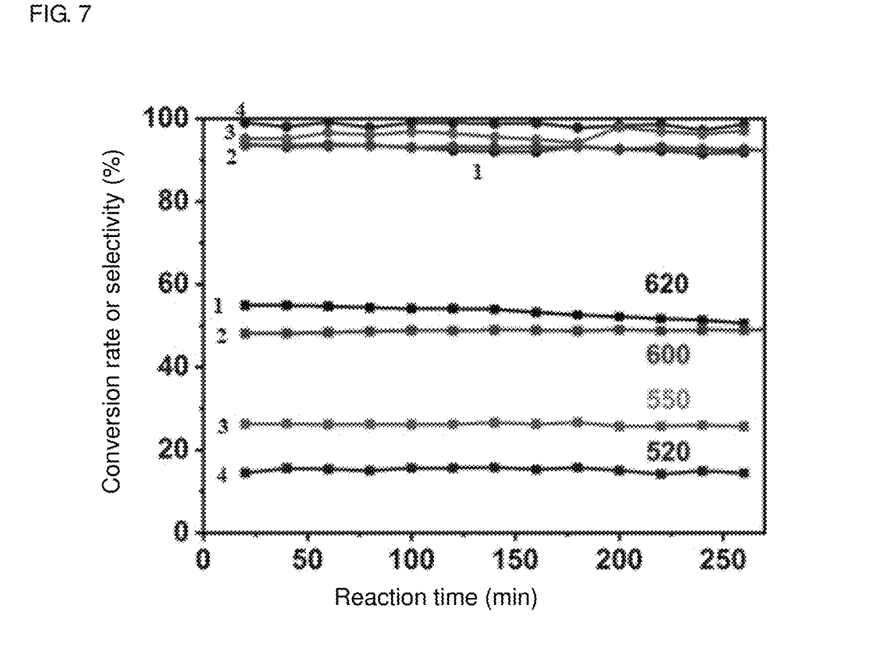
FIG. 7 illustrates a test curve chart of influence of different reaction temperature on catalytic activity in the embodiments of the present application, wherein curves at an upper position correspond to propylene selectivity and curves at a lower position correspond to propane conversion rate.

(4) For the influence of the reaction temperature on the catalytic activity of the PtZn/SiO$_2$ catalyst, refer to FIG. 7. The reaction conditions are the same as those in the embodiments 1, 7, 8 and 9. It can be seen from FIG. 7 that, with the increase of the reaction temperature, the propane conversion rate increases gradually, but the propylene selectivity decreases, and the best conversion rate and selectivity are obtained at 600° C.

Figure 8:
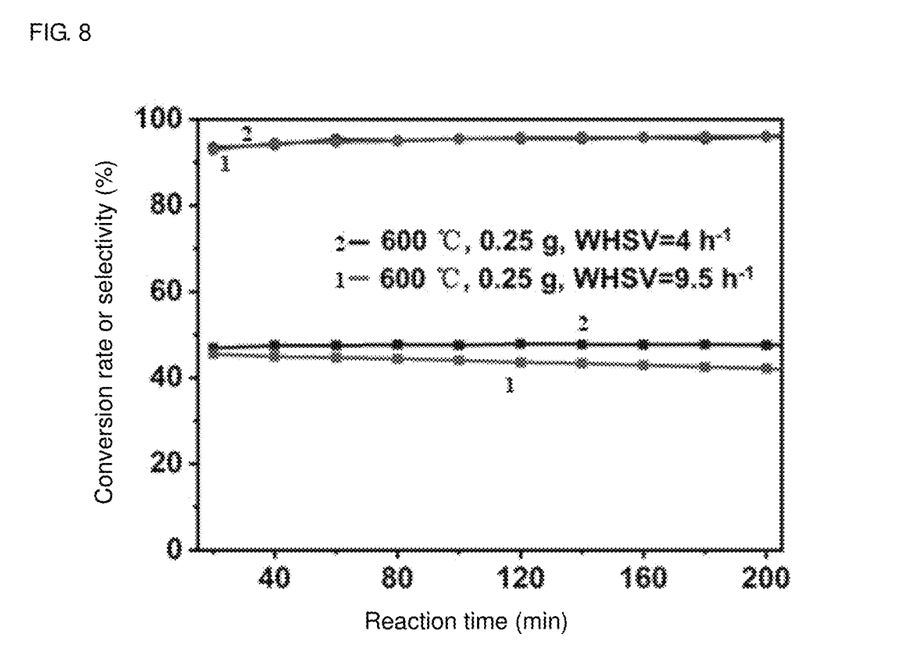
FIG. 8 illustrates a test curve chart of influence of different propane space velocities on catalytic activity in the embodiments of the present application, wherein curves at an upper position correspond to propylene selectivity and curves at a lower position correspond to propane conversion rate.

(5) For the influence of the propane space velocity on the propane dehydrogenation activity, refer to FIG. 8. The reaction conditions are the same as those in the embodiments 1 and 10. It can be seen from FIG. 8 that, with the increase of the propane space velocity, the propane conversion rate decreases, so the optimum space velocity is 4 $h^{-1}$.

Figure 9:
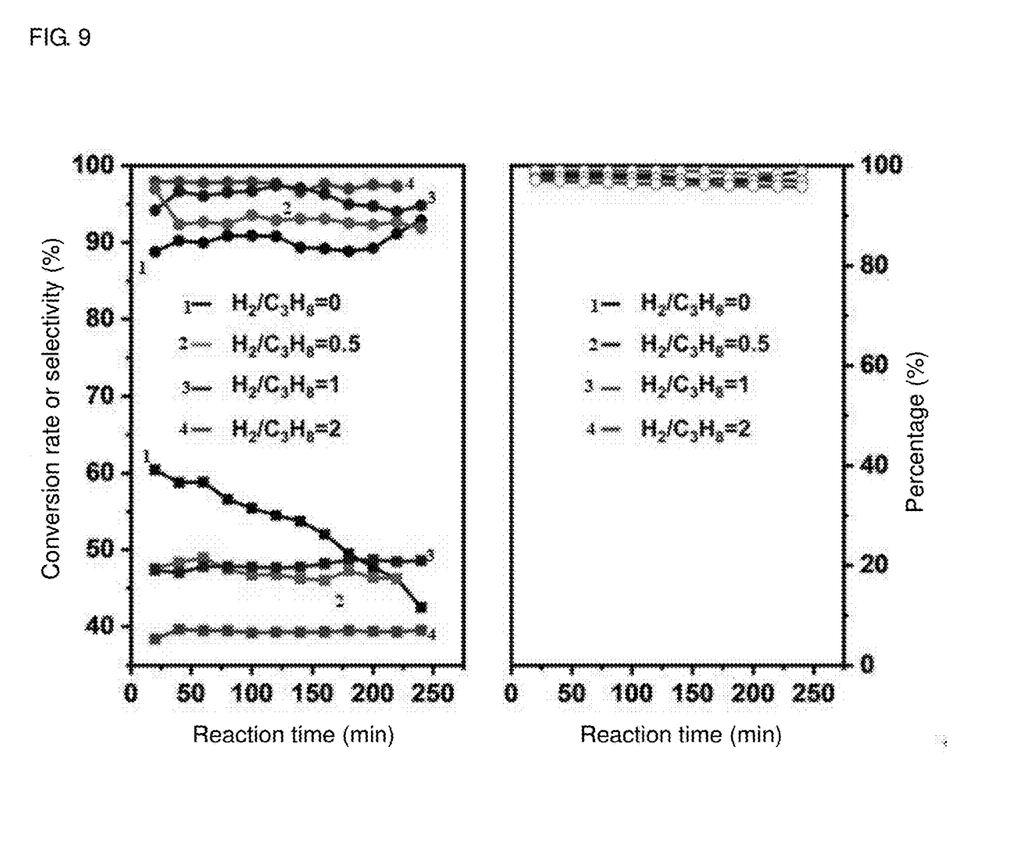
FIG. 9 illustrates a test curve chart of influence of different propane/hydrogen ratios on catalytic activity in the embodiments of the present application, wherein curves at an upper position correspond to propylene selectivity and curves at a lower position correspond to propane conversion rate.

(6) For the influence of the ratio of propane to hydrogen on the propane dehydrogenation activity, refer to FIG. 9. The reaction conditions are the same as those in the embodiments 1, 11, 12 and 13. It can be seen from FIG. 9 that, with the increase of H$_2$:C$_3$H$_8$, the propane conversion rate decreases slightly, but the propylene selectivity increases significantly, which indicates that H$_2$ partial pressure has a significant influence on the propane dehydrogenation reaction, and the optimum ratio of propane to hydrogen is 1.

The preparation of the catalyst in the present application can be realized by adjusting the process parameters according to the content of the present application, and the performance basically consistent with the examples is shown in the tests. The present application has been exemplarily described above. It should be noted that, without departing from the core of the present application, any simple deformation, modification or equivalent replacement by those skilled in the art without contributing any inventive labor should fall into the scope of protection of the present application.

What is claimed is:

1. A process for the dehydrogenation of an alkane to prepare an alkene, comprising reacting the alkane in the presence of a supported PtZn intermetallic alloy catalyst to produce the alkene, wherein the alkane comprises ethane, propane, and/or butane; wherein the supported PtZn intermetallic alloy catalyst comprises Pt as an active component and Zn as a promoter; wherein said Pt and Zn are supported on a support and form an atomically ordered intermetallic alloy; and wherein, based on the weight of the support in the catalyst, the weight percentage of Pt is no more than 1 wt %, and the weight percentage of Zn is no more than 1.7 wt %.

2. The process according to claim 1, wherein the alkene is propylene and the alkane is propane; and wherein the dehydrogenation of the alkane is carried out according to the following steps:
   tableting the supported PtZn intermetallic alloy catalyst into a granular catalyst with a mesh size of 20-40 meshes;
   putting the obtained granular catalyst into a fixed bed reactor, feeding with nitrogen, and then heating the temperature to a pretreatment temperature of 500-700° C.;
   performing pretreatment with hydrogen, maintaining the temperature at the pretreatment temperature for 0.5h-1h, and then tuning the temperature to a reaction temperature of 500-650° C.; and
   performing reaction with a reaction gas comprising propane and hydrogen;
   wherein the molar ratio of hydrogen to propane is (0-2):1, nitrogen is an equilibrium gas, the total gas amount is kept unchanged, and the reaction space velocity based on propane is 1-5$h^{-1}$.

3. The process according to claim 1, wherein the weight percentage of Pt is 0.025 wt %-1 wt %.

4. The process according to claim 1, wherein the weight percentage of Zn is 0.025 wt %-1.5 wt %.

5. The process according to claim 1, wherein the support is one selected from the group consisting of silicon dioxide, molecular sieve, zeolite, and aluminum oxide.

* * * * *